United States Patent [19]
Löser et al.

[11] Patent Number: 5,927,275
[45] Date of Patent: Jul. 27, 1999

[54] VALVE FOR A RESPIRATOR

[75] Inventors: Ralf-Ernst Löser; Bernhard Ludwig, both of Lübeck, Germany

[73] Assignee: Drägerwerk AG, Lübeck, Germany

[21] Appl. No.: 08/926,233

[22] Filed: Sep. 10, 1997

[30] Foreign Application Priority Data

Mar. 20, 1997 [DE] Germany ............................ 197 11 595

[51] Int. Cl.$^6$ .................................................. A61H 16/00
[52] U.S. Cl. ............................... 128/205.24; 128/204.21; 128/204.22
[58] Field of Search .................. 128/205.24, 205.25, 128/204.23, 204.22, 204.21, 205.11, 207.12, 200.24, 203.12

[56] References Cited

U.S. PATENT DOCUMENTS 5,758,641  6/1998  Karr .................................. 128/204.22
5,813,399  9/1998  Isaza et al. ........................ 128/204.21

FOREIGN PATENT DOCUMENTS 8417946  11/1984  France ............................... 128/205.24
25 73 658  5/1986  France .

*Primary Examiner*—John Weiss
*Assistant Examiner*—Charles W. Anderson
*Attorney, Agent, or Firm*—McGlew and Tuttle

[57] ABSTRACT

A valve for a respirator with a closing member, which is located at a valve seat 6 and is actuated by an electric drive 12, is improved in terms of its dynamic properties. A detector for detecting a first electric signal present at the moving drive a simulator for simulating a second electric signal generated at the nonmoving drive are provided. A comparator forms a differential signal between the first electric signal and the second electric signal. A closed action (feed back loop) circuit sets the position of the closing element in relation to the valve seat according to a preset valve $p_s$. The differential signal is applied to the control circuit are provided.

11 Claims, 3 Drawing Sheets

VALVE FOR A RESPIRATOR

FIELD OF THE INVENTION

The present invention pertains to a valve for a respirator with a valve housing which has a gas inlet and a gas outlet and has a valve space with a valve seat and a valve chamber, with a closing element, which is located at the valve seat and separates the valve space from the valve chamber, with an electric drive, which actuates the closing element and is connected to a control device, and with a closed action circuit for setting the position of the closing element in relation to the valve seat according to a preset value.

BACKGROUND OF THE INVENTION

A valve of this type has become known from FR 25 73 658. The pressure in an expiration line of a respirator is maintained at a predetermined value in this known valve by means of a diaphragm valve actuated by a moving coil drive. The actual value of the pressure in the expiration line is measured for this purpose at the gas inlet of the valve and is compared with a preset value. Depending on the deviation of the actual value from the preset value, the diaphragm is lifted off from the valve seat more or less by the moving coil drive.

The drawback of this valve is the limited dynamic range and the tendency to vibrate with a pronounced resonance point. This makes it difficult to use the valve for forms of respiration in which great fluctuations may occur in the expiration pressure, e.g., in the case of assisted spontaneous respiration.

SUMMARY AND OBJECTS OF THE INVENTION

The primary object of the present invention is to improve a valve of the above-described type in terms of its dynamic properties.

The object is accomplished by means for detecting a first electric signal $U_1$ present at the moving drive, means for simulating a second electric signal $U_2$ generated at the nonmoving drive, a comparator for forming a differential signal $U_d$ between the first electric signal $U_1$ and the second electric signal $U_2$ and means for applying the differential signal to the action circuit.

The advantage of the present invention is essentially the fact that a marked improvement in the dynamic behavior of the valve is achieved by utilizing the differential signal generated by the change in the position of the drive for setting the position of the closing element in relation to the valve seat, without an additional, passive or active displacement or velocity transducer having to be arranged at the moving part of the drive. The determination and the comparison of the changed position of the drive with the reference position may be performed, e.g., in a simple manner in a computer, in which the electrical magnitudes, e.g., the ohmic resistance and the inductance of the drive located in the reference position, are simulated by means of software.

A moving coil drive or a Lifting magnet drive is especially suitable for use as an electric drive. Both the moving coil drive and the lifting magnet drive can be specified in the electric equivalent circuit diagram as a series-connected arrangement of an ohmic resistance, an inductance and an equivalent power source. The inductance changes during the change in the position of the moving part of the drive, and a voltage is additionally induced in the winding in a velocity- and position-dependent manner. The changes in the inductance and voltage are essentially linear in the case of a moving coil drive, while nonlinear components will additionally appear in the case of a lifting magnet. The changes in inductance and voltage in relation to a reference position, in which the drive assumes a defined reference position, e.g., a resting position, are considered.

In a preferred variants the electric drive is designed as a piezo drive, in which the charge Q changes in proportion to the deflection. The electric equivalent circuit diagram of the piezo drive comprises a parallel-connected arrangement of an ohmic resistance with a capacitance. The comparison of the electric signals of the moving piezo drive with the nonmoving drive may be carried out especially preferably in a measuring bridge, in which the corresponding branch of the bridge belonging to the piezo drive contains the components of the electric equivalent circuit diagram of the nonmoving piezo drive.

It is especially advantageous to also carry out the comparison of the electric signals of the nonmoving moving coil drive with the moving coil drive in a measuring bridge, in which the corresponding branch of the bridge belonging to the moving coil drive has the inductance $L_s$ and the ohmic resistance $R_s$ of the nonmoving moving coil drive, so that there is an equilibrium between the branches of the bridge in the state of rest and the voltage on the bridge diagonal assumes a minimum. A differential voltage, which is proportional to the velocity of deflection of the moving coil drive, appears on the bridge diagonal during the movement of the moving coil drive. This differential voltage is also introduced into the closed action circuit for setting the position of the closing element in relation to the valve seat.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
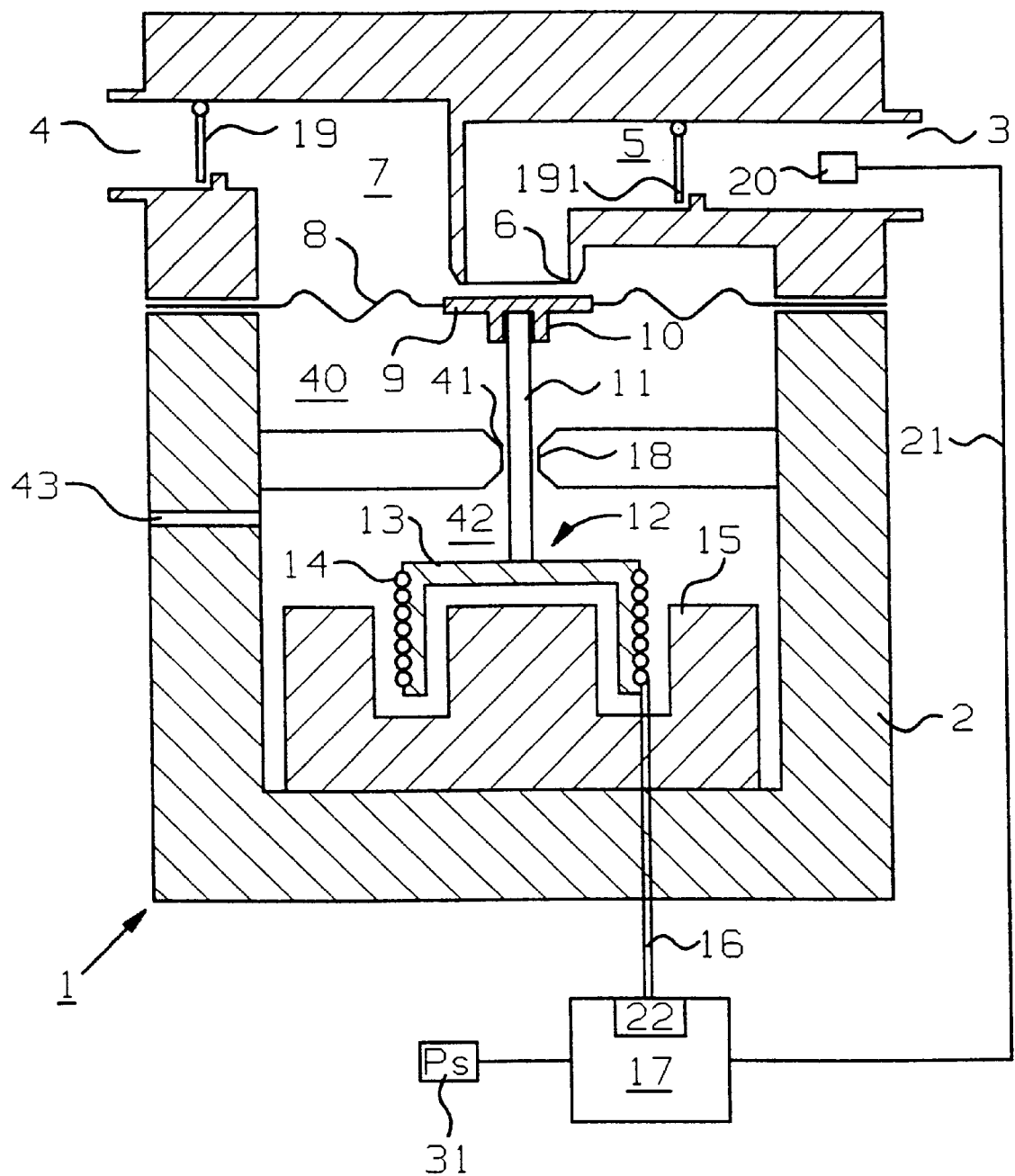
FIG. 1 is a longitudinal sectional view of a valve.

FIG. 1 shows the longitudinal section of an expiration valve 1 for a respirator, not shown in FIG. 1. The expiration valve 1 comprises a valve housing 2 with a gas inlet 3 and a gas outlet 4, with a valve space 5 with a valve seat 6, which said valve space is connected to the gas inlet 3, and a valve chamber 7 connected to the gas outlet. Opposite the valve seat 6, a closing element 9 is arranged at a control diaphragm 8 clamped into the valve housing 2. A gas flow from the valve space 5 into the valve chamber 7 can be throttled or even completely interrupted with the closing element 9. The underside of the closing element 9 is connected to a tappet 11 of a moving coil drive 12. The moving coil drive 12 comprises a pot-shaped coil former 14 connected to the tappet 11, with a moving coil 14 and a pot-shaped magnet 15. The lines 16 originating from the moving coil 14 are connected to a first measuring bridge 22 within a control device 17. The tappet 11 is guided axially in a pain bearing bush 18. Depending on the value of the current fling through and the direction of the current through the moving coil 14, the closing element 9 is pressed more or less strongly against the valve seat 6, or it is completely lifted off from the valve seat 6, so that a nearly unthrottled flow of gas is now possible from the gas inlet 3 to the gas outlet 4. A nonreturn valve 19 is arranged between the valve chamber 7 and the gas outlet 4 in order to prevent the flow of gas from the gas outlet 4 back into the valve chamber 7. As an alternative or in addition, a second nonreturn valve 191 may be arranged within the valve space 5. A pressure gauge 20 for determining the dynamic pressure generated by the closing element 9 within the valve space 5, which pressure gauge is connected to the control unit 17 via a line 21, is provided within the valve space 5.

The control diaphragm 8 and the plain bearing bush 18 surround a diaphragm chamber 40, which is in flow connection with an equalizing chamber 42 located in the area of the moving coil drive 12 via a gap 41 located between the plain bearing bush 18 and the tappet 11. The equalizing chamber 42 is open toward the environment via a hole 43. The pressure in the diaphragm chamber 40 changes during the movement of the control diaphragm 8 as a consequence of the lifting movement of the tappet 11, so that gas is either drawn in from the equalizing chamber 42 via the gap 41, or gas escapes into the equalizing chamber 42 via the gap 41 for pressure equalization. This brings about a damping of the control diaphragm 8. The extent of the damping can be set by adjusting the opening cross section and the length of the gap 41.

Figure 2:
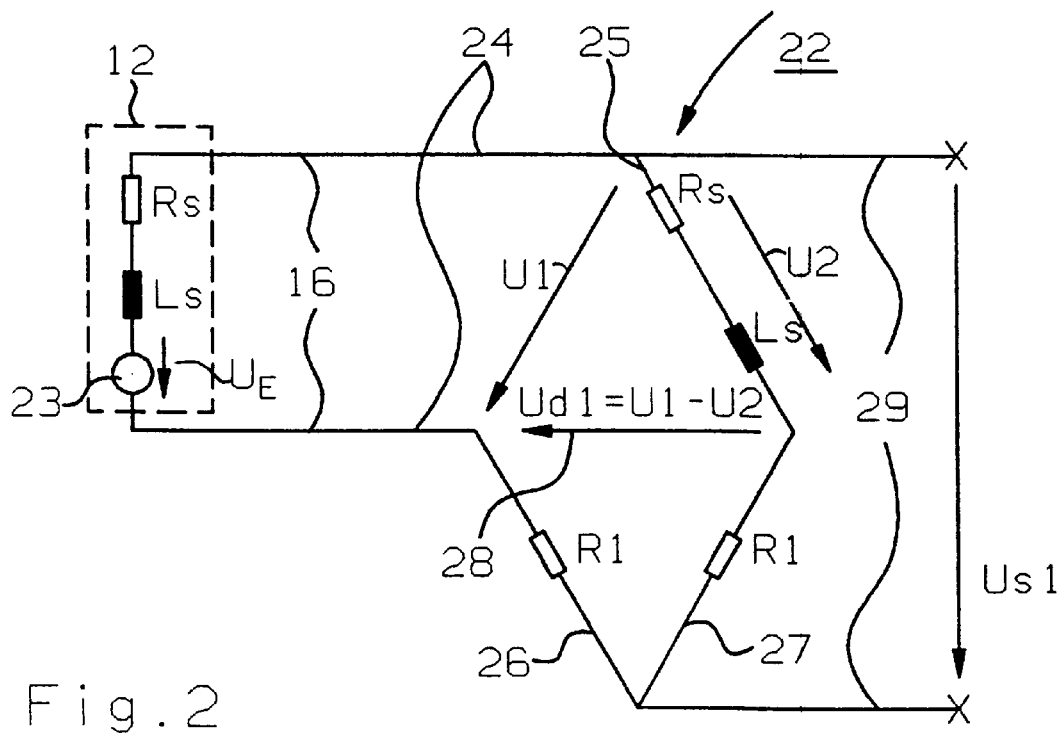
FIG. 2 is a moving coil drive connected to a measuring bridge.

FIG. 2 shows an electric equivalent circuit diagram of the moving coil drive 12 in conjunction with a first measuring bridge 22. A control voltage $U_{s1}$ is applied to the first bridge diagonal 29 of the first measuring bridge 22. The current within the moving coil 14 and consequently the position of the closing element 9 in relation to the valve seat 6 change as a function of $U_{s1}$. The moving coil drive 12 may be represented in the equivalent circuit diagram as an ohmic resistance $R_s$, an inductance $L_s$, and an equivalent power source 23 with the voltage $U_E$.

The voltage $U_E$ is proportional to the velocity of the tappet 21 in relation to the valve housing 2 or of the closing element 9 in relation to the valve seat 6, while $R_s$ and $L_s$ are related to the nonmoving moving coil drive 12. The resistance $R_s$, the inductance $L_s$, and the equivalent power source 23 together form a first bridge branch 24 of the first measuring bridge 22. An ohmic resistance $R_s$ and an inductance $L_s$, which are simulated according to the corresponding elements of the first bridge branch 24, are likewise provided in a second bridge branch 25 of the first measuring bridge 22. A third bridge branch 26 and a fourth bridge branch 27 are designed as ohmic resistances R. The voltage $U_1$ generated is the first electric signal on the first bridge branch 24, and the voltage $U_2$ generated is the second electric signal on the second bridge branch 25. A voltage $U_{d1}$, which is the differential signal of $U_1$ and $U_2$, is generated on a second bridge diagonal 28. $U_{d1}=0$ in the state of rest of the moving coil drive 12, because the voltage $U_E$ equals zero. A mutual induction voltage $U_E$ is generated at the moving coil drive 12 during the movement of the coil former 13 in relation to the pot-shaped magnet 25, and a voltage $U_{d1}$, which is proportional to the velocity of the coil former 13 in relation to the pot-shaped magnet 15, is obtained on the second bridge diagonal 28. The voltage $U_{d1}$ is applied as an interference variable to a control circuit 30 containing the moving coil drive 12 in order to achieve a rapid and low-vibration setting of the closing member 9 in relation to the valve seat 6.

Figure 3:
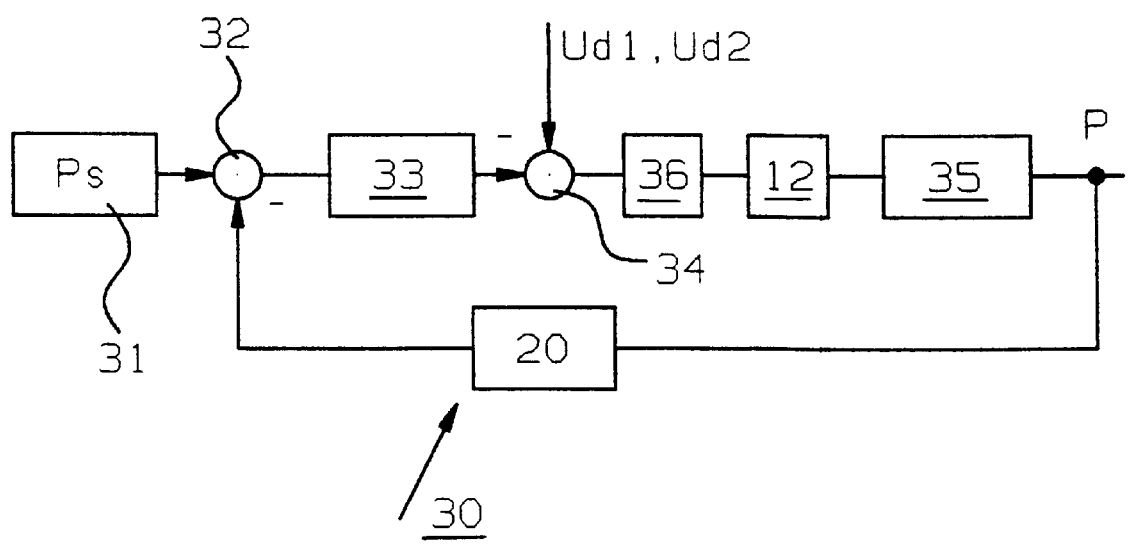
FIG. 3 is a control circuit for the measuring bridge of the valve according to FIG. 1.

This control circuit 30 is illustrated in FIG. 3. A pressure set point $p_s$, which shall become established within the valve space 5, is set with a set point setter 31. If the gas inlet 3 is connected to an expiration tube, not shown in the figure, the pressure set point $p_s$ is the PEEP (peak-end expiratory pressure) set on the respirator. The actual value of the pressure within the valve space 5 is measured with the pressure gauge 20. The difference between the pressure set point $p_s$ and the actual value is formed at a comparison point 32. The control circuit 30 comprises the comparison point 32, a first controller 33, a subtraction point 34 for applying $U_{d1}$, a second controller 36, the moving coil drive 12 as the adjusting member, a control system 35, which contains the valve space 5, and the pressure gauge 20, which measures the actual value of the pressure p in the valve space 5.

Figure 4:
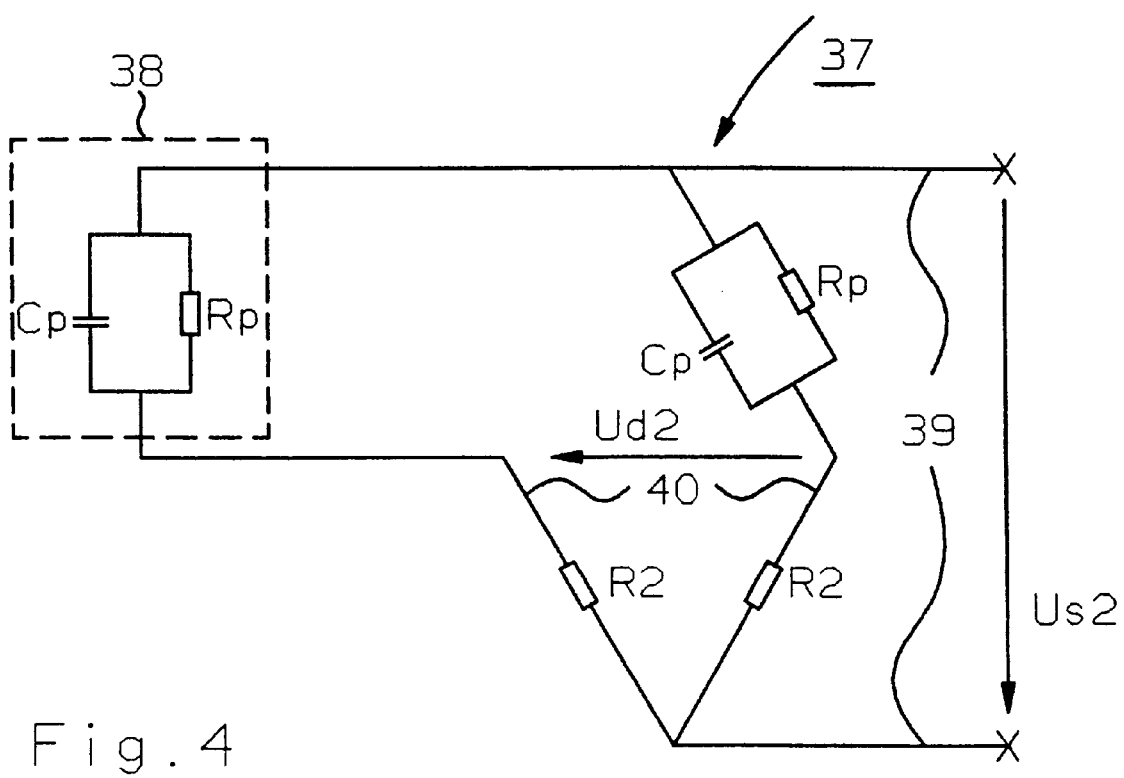
FIG. 4 is a piezo drive connected to a measuring bridge.

FIG. 4 schematically shows a piezo drive 38, which is connected to a second measuring bridge 37 and whose electric equivalent circuit diagram is a parallel-connected arrangement of a capacitance Cp with an ohmic resistance Rp. The bridge branch of the second measuring bridge 37 corresponding to the piezo drive 38 likewise contains the parallel-connected arrangement of the capacitance Cp with the ohmic resistance Rp. A control voltage $U_{s2}$ is applied to a first bridge diagonal 39, and a differential signal $U_{d2}$ proportional to the position or the velocity of the deflected piezo drive 38 is formed over a second bridge diagonal 40. In the state of the rest of the piezo drive 38, the differential signal $U_{d2}$ is equal to zero. The differential pressure voltage $U_{d2}$ may be applied, as an alternative to the differential voltage $U_{d1}$, to the control circuit 30, FIG. 3, at the subtraction point 34.

While specific embodiments of the invention have been shown and described in detail to illustrate the application of the principles of the invention, it will be understood that the invention may be embodied otherwise without departing from such principles.

What is claimed is:

1. A respirator valve, comprising:

a valve housing with a gas inlet and a gas outlet and a valve space with a valve seat and a valve chamber;

a closing element located at the valve seat for separating the valve space from the valve chamber;

an electric drive actuating said closing element, said electric drive being connected to a control device, said electric drive including a closed action circuit for setting a position of said closing element in relation to said valve seat according to a preset value;

detection means for detecting a first electric signal $U_1$ present at said electric drive during movement of said electrical drive;

simulation means for simulating a second electric signal $U_2$ generated at said electrical drive during nonmovement at a reference position;

a comparator for forming a differential signal $U_d$ from the first electric signal $U_1$ and the second electric signal $U_2$; and means for applying the differential signal $U_d$ to said action circuit.

2. The valve in accordance with claim 1, wherein said electric drive is one of a piezo electric drive and a lifting magnet drive, besides a moving coil drive.

3. The valve in accordance with claim 1, wherein said comparator includes a measuring bridge provided for forming said differential signal $U_d$ from said first electric signal $U_1$ and said second electric signal $U_2$.

4. The valve in accordance with claim 1, further comprising: a nonreturn valve disposed between said gas inlet and said gas outlet for interrupting a flow of gas from said gas outlet to said gas inlet.

5. The valve in accordance with claim 1, further comprising: a diaphragm chamber arranged opposite said valve chamber; a control diaphragm connected to said closing element, said diaphragm chamber being separated from said valve chamber by said control diaphragm and having a throttling element open toward an equalizing chamber and/or to the ambient atmosphere.

6. A respirator valve, comprising:
- a valve housing with a gas inlet and a gas outlet and a valve space with a valve seat and a valve chamber;
- a closing element located at the valve seat, said closing element being movable between an open position and a position for separating the valve space from the valve chamber;
- an electric drive actuating said closing element, said electric drive being connected to a control device, said control device including a feed back loop for setting a position of said closing element in relation to said valve seat according to a preset value;
- detection means for detecting a first electric signal $U_1$ present at said electric drive during movement of said electric drive;
- simulation means for simulating a second electric signal $U_2$ generated at said electrical drive during nonmovement of said electric drive;
- a comparator for forming a differential signal $U_d$ from the first electric signal $U_1$ and the second electric signal $U_2$; and
- means for applying the differential signal $U_d$ to said feed back loop.

7. The valve in accordance with claim 6, wherein said electric drive is one of a piezo electric drive and a lifting magnet drive, besides a moving coil drive.

8. The valve in accordance with claim 6, wherein said comparator includes a measuring bridge provided for forming said differential signal $U_d$ from said first electric signal $U_1$ and said second electric signal $U_2$.

9. The valve in accordance with claim 6, further comprising: a nonreturn valve disposed between said gas inlet and said gas outlet for interrupting a flow of gas from said gas outlet to said gas inlet.

10. The valve in accordance with claim 6, further comprising: a diaphragm chamber arranged opposite said valve chamber; a control diaphragm connected to said closing element, said diaphragm chamber being separated from said valve chamber by said control diaphragm and having a throttling element open toward an equalizing chamber or to the ambient atmosphere.

11. The valve in accordance with claim 6, further comprising: a diaphragm chamber arranged opposite said valve chamber; a control diaphragm connected to said closing element, said diaphragm chamber being separated from said valve chamber by said control diaphragm and having a throttling element open toward an equalizing chamber and to the ambient atmosphere.

* * * * *